US007432526B2

United States Patent
Van de Walle et al.

(10) Patent No.: US 7,432,526 B2
(45) Date of Patent: Oct. 7, 2008

(54) SURFACE-PASSIVATED ZINC-OXIDE BASED SENSOR

(75) Inventors: Christian G. Van de Walle, Santa Barbara, CA (US); Peter Kiesel, Palo Alto, CA (US); Oliver Schmidt, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 118 days.

(21) Appl. No.: 11/314,881

(22) Filed: Dec. 20, 2005

(65) Prior Publication Data

US 2007/0138464 A1    Jun. 21, 2007

(51) Int. Cl.
*H01L 29/10* (2006.01)

(52) U.S. Cl. .................... 257/43; 257/798; 438/85; 338/1; 338/223

(58) Field of Classification Search ........... 257/43, 257/798; 438/85; 338/1, 223
See application file for complete search history.

(56) References Cited

U.S. PATENT DOCUMENTS 5,780,898 A * 7/1998 Tamaki et al. ............... 257/331
2004/0026736 A1 * 2/2004 Grupp et al. ................ 257/330
2004/0058463 A1 * 3/2004 Nause et al. .................. 438/22

OTHER PUBLICATIONS

Koike et al. (Applied Physics Letters, 87, 112106 (2005).*
The Periodic Table of the Elements, the International Union of Pure and Applied Chemistry (IUPAC), available at http://www.iupac.org/reports/periodic_table, Oct. 3, 2005.*
Oliver Schmidt, Peter Kiesel, Chris G. Van de Walle, Noble M. Johnson, Jeff Nause and Gottfried H. Döhler, "Evidence for an electrically conducting layer at the native zinc oxide surface," *Jpn. J. Appl. Phys.* Part 1, vol. 44, 7271-7274 (2005) (published Oct. 11, 2005).
Oliver Schmidt, Arnd Geis, Peter Kiesel, Chris G. Van de Walle, Noble M. Johnson, Andrey Bakin, Andreas Waag and Gottfried H. Döhler, "Analysis of a Conducting Channel at the Native Zinc Oxide Surface," *Superlattices and Microstructures*, 39 (2006) 8-16.

* cited by examiner

*Primary Examiner*—Jerome Jackson
*Assistant Examiner*—Jami M Valentine
(74) *Attorney, Agent, or Firm*—Marger Johnson & McCollom, PC

(57) ABSTRACT

A semiconductor device has a heterostructure including a first layer of semiconductor oxide material. A second layer of semiconductor oxide material is formed on the first layer of semiconductor oxide material such that a two dimensional electron gas builds up at an interface between the first and second materials. A passivation layer on the outer surface stabilizes the structure. The device also has a source contact and a drain contact.

20 Claims, 2 Drawing Sheets

SURFACE-PASSIVATED ZINC-OXIDE BASED SENSOR

GOVERNMENT FUNDING

This invention was made with Government support under Contract No. F49620-02-01-0343, issued by the Air Force Office of Scientific Research. The Government has certain rights in this invention.

BACKGROUND

Semiconductor devices include transistors. A transistor may modulate a current flowing through it in response to an input signal. One example of a type of a transistor is a field effect transistor (FET). An FET may change the characteristics of a channel in response to the input signal. The input signal affects the characteristics of the channel such as the carrier concentration and the carrier type. By affecting the characteristics of the channel, the input signal may modulate current flowing through the channel, and hence, flowing through the transistor. Typically, such a transistor may include a source and a drain coupled to the channel. A gate receives the input signal to modulate the channel.

Heterostructure FETs (HFETs) are FETs manufactured out of at least two different semiconductor materials, hence a 'hetero' structure rather than a homogenous one. The use of zinc oxide (ZnO) has promising potential for sensors. Zinc oxide reacts to its surrounding environment. The carrier concentration in the channel of the HFET may be controlled by the surrounding environment, allowing the zinc oxide to act as a 'chemical gate.'

However, bare zinc oxide surfaces may have stability issues that result in its difficulties to withstand typical environments in which gas or liquid sensors operate. Additionally, zinc may escape from the surface, contaminating or detrimentally affecting biosensors.

SUMMARY

A semiconductor device has a heterostructure including a first layer of semiconductor oxide material. A second layer of semiconductor oxide material is formed on the first layer of semiconductor oxide material such that a two dimensional electron gas builds up at an interface between the first and second materials. A passivation layer on the outer surface stabilizes the structure. The device also has a source contact and a drain contact.

A semiconductor device may be manufactured by providing a substrate and then growing a first layer of semiconductor oxide material. A second layer of semiconductor oxide material is grown on the first layer of semiconductor oxide material such that a two dimensional electron gas will form at an interface between the first and second layers. A passivation layer is formed on an outer surface of a structure formed of the first and second layers. Source and drain contacts are provided to contact the two dimensional electron gas.

DETAILED DESCRIPTION

Figure 1:
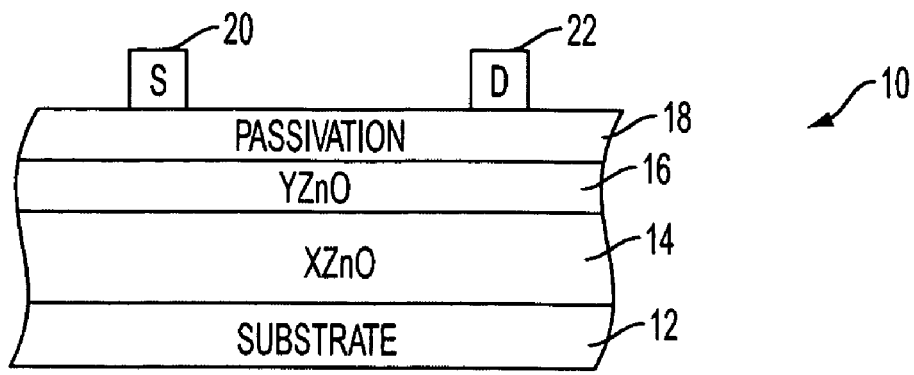
FIG. 1 shows an embodiment of a heterostructure field effect transistor with a chemical gate.

FIG. 1 shows a semiconductor device 10 having the functionality of a heterostructure field effect transistor (HFET). The HFET in this embodiment has a structure formed of two layers of semiconductor oxide materials. Depending upon the materials selected, use of a heterostructure may cause a two dimensional electron gas (2DEG) to form at the interface between the two layers. These gases are very sensitive to the properties of their surface, making them promising structures for sensors.

The sensitivity of 2DEGs leads to changes in the carrier concentration in a channel formed in the heterostructure between the source and drain contacts. The changes in the carrier concentration may be detected, allowing sensitive detection of changes in the properties of the surface of the HFET. The change may be due to exposure to particular substances. For example, biosensors or chemical sensors may detect the presence of certain molecules or ions, such as sodium, calcium, chlorine, oxygen, or carbon dioxide, substances such as glucose or cholesterol, or certain enzymes.

Some investigation has occurred into nitride semiconductors for sensing applications. However, nitride semiconductors are not biocompatible. Oxide layers grown on the surface to render them biocompatible severely diminish the sensitivity of the sensors. Oxide-based wide-band-gap semiconductors, such as zinc oxide, may have several advantages over the nitrides. Early results revealed that zinc oxide was cytotoxic, killing cells. A plausible explanation for this is that zinc escapes from the surface of a layer of zinc oxide and the zinc is what destroys the cell. Therefore, it appears that a bare zinc oxide surface is problematic to be used in a biocompatible sensor.

With the use of surface passivation, these limitations may be overcome. Passivation layers must be very thin and not interfere with the sensitivity of the sensor. Using silicon as a passivation layer fulfills this role. The presence of small amounts of silicon renders the surface very resistant to etching. Zinc oxide is normally etched readily in wet etching, but the presence of silicon on the surface severely reduces the etch rate.

The device 10 shown in FIG. 1 has a structure formed of a first and second layer of semiconductor oxide material. In this particular embodiment, the first layer 14 is a layer of zinc oxide alloy grown upon a substrate 12. In general, the layers in all of the illustrated structures do not have to be a ZnO layer could be a combination of different ZnO alloys. For example, one could form the electron gas also with one layer of CdZnO and one layer of MgZnO. This is shown in FIG. 1 as two layers, one of an alloy of X and zinc oxide, and one of an alloy of Y and zinc oxide. X and Y may be cadmium, magnesium, or nothing, where the layer is just zinc oxide. In addition, X may be one concentration of one material, and Y may be another concentration of the same material. Several different substrates may be used including zinc oxide wafers, silicon, sapphire, cadmium, epitaxially grown gallium nitride, silicon carbide, and $ScAlMgO_4$ (SCAM).

The second layer of semiconductor oxide material 16 is formed on the first layer such that a two dimensional electron gas builds up at an interface between the two layers. In this embodiment, the second layer is a zinc oxide alloy, such as magnesium zinc oxide (MgZnO), cadmium zinc oxide (CdZnO) or magnesium cadmium zinc oxide (MgCdZnO). These materials are only for example. The oxide layer could be any wide-band gap semiconductor oxide. The second layer may be formed of any semiconductor oxide alloy that has a band gap larger than the first layer. In one particular example, a MgZnO layer was formed with a Mg content of 5% or higher. This leads to a sufficient offset that resulted in the formation of a two dimensional electron gas. Due to the polarization fields in this material system, this gas will form regardless of doping in contrast to other material systems like GaAs/AlGaAs. The carriers in the gas are highly sensitive to the condition of the surface. These aspects render these structures desirable as sensors.

The 2DEG is utilized in a transistor fashion by using the source 20 and the drain 22.

A passivation layer 18 prevents the zinc from escaping the surface, rendering the sensor biocompatible, as well as preserving the sensitivity of the sensor. Other passivation materials may include dielectric materials such as silicon oxides, silicon nitrides, and silicon oxynitrides.

As described in co-pending U.S. patent application Ser. No. 11/343,341 incorporated herein by reference the electrical properties of zinc oxide (ZnO) bulk and epi-samples might be strongly influenced by the sample ambient. A conducting electron channel at the ZnO surface is present under certain conditions. A variety of surface passivation layers and coatings have been investigated in order to preserve or avoid the surface conducting channel under either environment.

The native electron accumulation layer would interfere with the artificial electron gas which is formed at the XZnO/YZnO (such as ZnO/MgZnO) interface. Therefore, in situations where the accumulation layer might occur, it is necessary to design the passivation layer such that it destroys or prevents the native accumulation layer. This can be achieved by exposure to air or an appropriate deposition of a passivation layer. A potentially present surface conductivity has to be destroyed prior or during the deposition of the passivation layer. In particular it might be useful to deposit monolayers or thin layers of dielectric materials in-situ with the semiconductor oxide deposition.

For example, this can be achieved by terminating the growth of a ZnO layer with one or a few monolayers in which Zn is replaced mostly by Si. Furthermore organic materials such as polyimide or self-assembled monolayer including alkylsiloxanes, fatty acids, and alkanethiolates are good candidates for the passivation coating.

Figure 2:
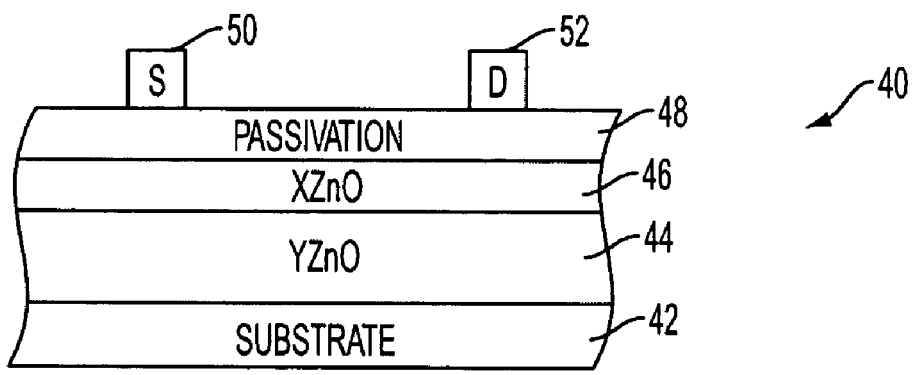
FIG. 2 shows an alternative embodiment of a heterostructure field effect transistor with a chemical gate.

Alternative structures and formations are of course possible. For example, FIG. 2 shows a device 40 in which the first semiconductor oxide material 44 on the substrate 42 is a zinc oxide alloy YZnO, where Y may be magnesium, cadmium, magnesium and cadmium together, and the second semiconductor oxide material XZnO 46 is zinc oxide or other material with ZnO, such as a different concentration of Mg. In this example the polarity of the substrate is different and therefore requires a different sequencing of the layers in order to form a carrier accumulation at the interface. The passivation layer 48 is then deposited on the second layer with the source 50 and the drain 52 being formed on the passivation layer. The ordering of the semiconductor oxide layers depends upon the desired polarity of the devices.

Figure 3:
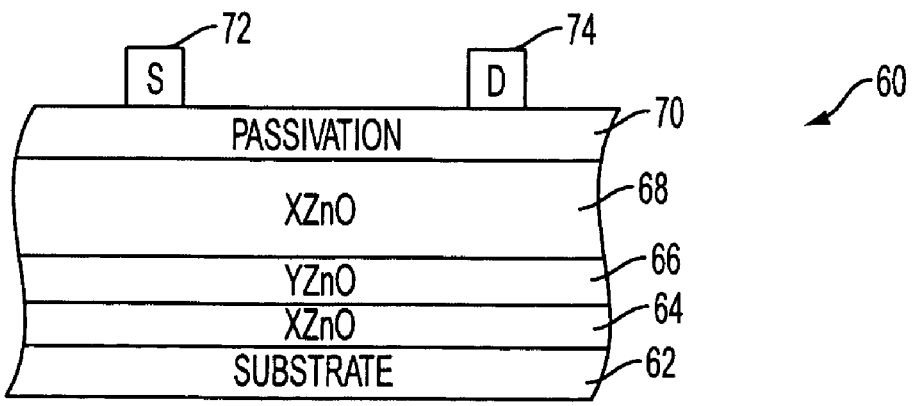
FIG. 3 shows an alternative embodiment of a heterostructure field effect transistor with a chemical gate.

Another alternative device is shown in FIG. 3 at 60. The substrate 62 has formed upon it a first semiconductor oxide layer (XZnO) 64, in this case zinc oxide. The second layer of semiconductor oxide material (YZnO) 66 is then formed on the first layer. In this embodiment, a third very thin layer is formed at 68, possibly from the same material as the first layer as shown, but not limited to that material. This may be desirable for better source and drain contacts, as well as other reasons. The passivation layer 70 is then formed on the third layer, upon which is then formed the source 72 and the drain 74.

It must be noted that the passivation layer is formed on the second layer in some embodiments and the third layer in others. It does not matter how many layers form the structure portion of the device. The passivation layer is formed on the outer layer of the structure, whether the outer layer is the second, third or other layer of the structure. Similarly, the ordering of the layers in a structure having more than two layers is not necessarily that the metal zinc oxide layer be sandwich between layers of zinc oxide. The alteration of the orders discussed with regard to FIG. 2 may also occur in the more-than-two layer structures.

Figure 4:
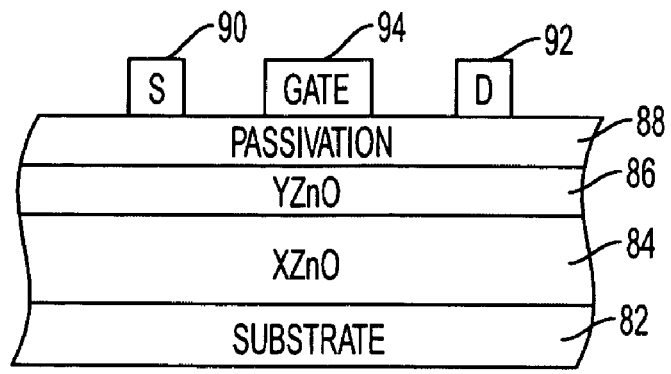
FIG. 4 shows an alternative embodiment of a heterostructure field effect transistor with a chemical gate.

Similarly, while the embodiments of FIGS. 1, 2 and 3 do not show a gate contact, it is possible that a gate contact may be formed on the structure, as shown in FIG. 4. In FIG. 4, device 80 has a structure formed on the substrate 82. In this particular embodiment, the first layer 84 is zinc oxide, but the different ordering discussed above may also apply here. The second layer 86 is the metal zinc oxide layer, with the passivation layer on the outer surface at 88. In addition to the source contact 90 and the drain contact 92, there is also a gate 94, typically formed of metal. The gate has to be large enough such that all current paths between source and drain and through the 2DEG are influenced by the gate area as it is well known for HFET design.

The use of the gate may allow the sensor to react to other types of substances that would otherwise be undetectable. For example, certain gases such as $H_2$ would not affect the surface of the other embodiments and would therefore be undetectable. If the metal of the gate is chosen carefully, it can act as a catalyst and cause dissociation of the $H_2$ that can then be detected. Different metals may be used to detect different gases.

Figure 5:
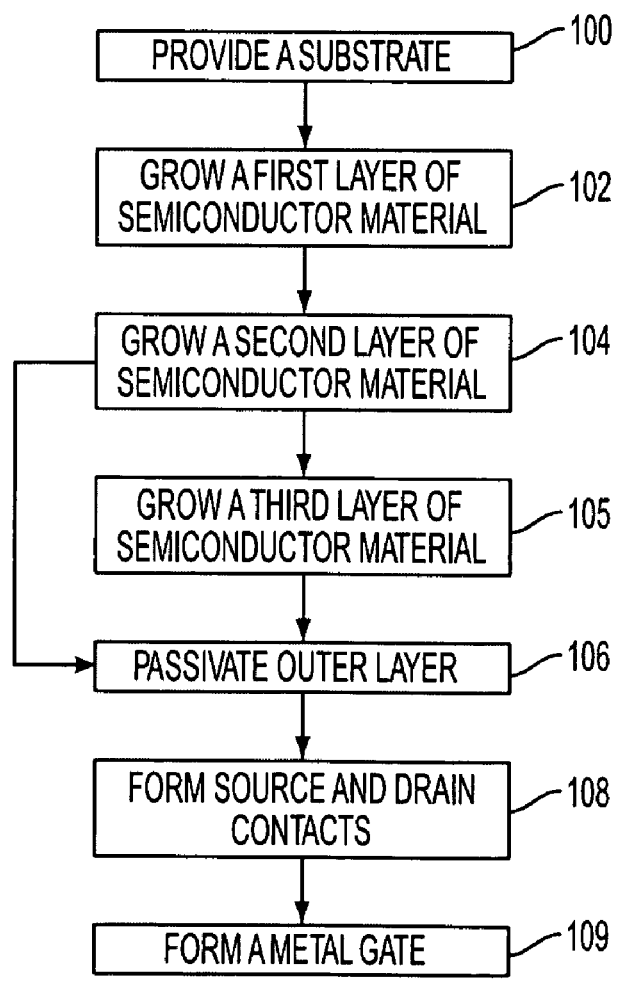
FIG. 5 shows a flowchart of an embodiment of a method of manufacturing a chemical gate heterostructure field effect transistor.

Having seen different embodiments, with many possible combinations and subcombinations possible between them, the discussion now turns to the manufacture of these devices. An embodiment of a manufacturing flow is shown in flowchart form in FIG. 5.

At 100, a substrate is provided. As previously discussed, the substrate may be sapphire, zinc oxide, cadmium, silicon carbide, SCAM and gallium nitride. At 102, the first layer of semiconductor oxide material is grown. As discussed above, the first layer may be the wide-band gap oxide such as ZnO or any alloy of the wide band gap semiconductor oxide such as MgZnO.

At 104, the second layer of semiconductor oxide material is grown on the first layer such that the two dimensional electron gas forms at the interface of the two layers. As discussed above, this may be controlled by the alloy mix in each layer.

At 106, the passivation layer is formed by any number of readily available techniques, including evaporation or chemical vapor deposition. With the strong bond between oxygen and silicon, obtaining a silicon passivation surface would seem fairly easy. As also discussed, the passivation layer may be formed from silicon nitrides, which would typically involved evaporation or depositing the silicon layer in the presence of nitrogen, and silicon oxynitrides from similar processes. In particular it might be useful to deposit monolayers or thin layers of dielectric materials in-situ after growth of the semiconductor oxide. For example, this can be achieved by terminating the growth of a ZnO layer with one or a few monolayers in which Zn is replaced mostly by Si. Another possibility is to form the passivation layer from self-assembled monolayers. The passivation layer is formed on the outer surface of the structure that is formed at least from the first and second layers. If the optional process of forming a third layer is performed at 105, the outer surface will be that of the third layer.

After the structure is passivated, the device is formed by the deposition of source and drain contacts at 108. Even though the passivation layer is supposed to be very thin it might be beneficial to remove the passivation layer at the areas where the contacts are supposed to be. This can be done using semiconductor processing steps such as lithography and etching. If a gate is desired, a metal gate is deposited and formed at 109, with the selection of the metal being possibly controlled by a desired gas dissociation that would be detectable by the sensor.

In this manner, a biocompatible sensor device may be formed that is stable in various environments but does not lose its sensitivity. Further, this sensor can be achieved with readily available semiconductor processes.

It will be appreciated that various of the above-disclosed and other features and functions, or alternatives thereof, may be desirably combined into many other different systems or applications. Also that various presently unforeseen or unanticipated alternatives, modifications, variations, or improvements therein may be subsequently made by those skilled in the art which are also intended to be encompassed by the following claims.

The invention claimed is:

1. A semiconductor device, comprising:
   a sensor structure, comprising:
      a first layer of semiconductor oxide material;
      a second layer of semiconductor oxide material formed on the first layer of semiconductor oxide material;
      a two dimensional electron gas at an interface between the first and second materials, the first and second layers of material arranged so as to allow the two dimensional electron gas to react to the environment; and
      a passivation layer on an outer surface of the structure;
   a source contact on one of either the outer surface or the passivation layer; and
   a drain contact on one of either the outer surface or the passivation layer.

2. The semiconductor device of claim 1, at least one of the first and second layers further comprising a layer of zinc oxide.

3. The semiconductor device of claim 1, at least one of the first and second layers further comprising a layer of a zinc oxide alloy.

4. The semiconductor device of claim 3, the zinc oxide alloy further comprising one selected from the group comprised of: MgZnO, CdZnO, MgCdZnO.

5. The semiconductor device of claim 1, the device further comprising a third layer comprised of zinc oxide.

6. The semiconductor device of claim 1, the passivation layer further comprising a layer of one of the group consisting of: silicon, silicon oxide, silicon nitride, silicon oxynitride.

7. The semiconductor device of claim 1, the passivation layer being sufficiently thin such that the passivation layer does not interfere with sensitivity of the first and second semiconductor oxide layers to a surrounding environment.

8. The semiconductor device of claim 1, the passivation layer further comprising a layer of one of the group consisting of: an organic compound, polyimide and a self-assembled monolayer.

9. The semiconductor device of claim 1, the device further comprising a metal gate.

10. The semiconductor device of claim 1, the structure is formed upon a substrate.

11. The semiconductor device of claim 10, the substrate further comprise one selected from the group consisting of: silicon, zinc oxide, cadmium, gallium nitride, silicon carbide, ScAlMgO and sapphire.

12. A semiconductor device, comprising:
   a sensor structure, comprising:
      a first layer of semiconductor oxide material;
      a second layer of semiconductor oxide material formed on the first layer of semiconductor oxide material;
      a two dimensional electron gas at an interface between the first and second materials to react to the environment; and
      a passivation layer on an outer surface of the structure, the passivation layer comprising a layer of one of the group consisting of: an organic compound, polyimide and a self-assembled monolayer;
   a source contact; and
   a drain contact.

13. The semiconductor device of claim 12, at least one of the first and second layers further comprising a layer of zinc oxide.

14. The semiconductor device of claim 12, at least one of the first and second layers further comprising a layer of a zinc oxide alloy.

15. The semiconductor device of claim 14, the zinc oxide alloy further comprising one selected from the group comprised of: MgZnO, CdZnO, MgCdZnO.

16. The semiconductor device of claim 12, the device further comprising a third layer comprised of zinc oxide.

17. The semiconductor device of claim 12, the passivation layer being sufficiently thin such that the passivation layer does not interfere with sensitivity of the first and second semiconductor oxide layers to a surrounding environment.

18. The semiconductor device of claim 12, the device further comprising a metal gate.

19. The semiconductor device of claim 12, the structure is formed upon a substrate.

20. The semiconductor device of claim 19, the substrate further comprise one selected from the group consisting of: silicon, zinc oxide, cadmium, gallium nitride, silicon carbide, ScAlMgO and sapphire.

* * * * *